United States Patent [19]

Brownlee et al.

[11] 4,348,387
[45] Sep. 7, 1982

[54] METHOD AND SYSTEM FOR THE CONTROLLED RELEASE OF BIOLOGICALLY ACTIVE SUBSTANCES TO A BODY FLUID

[75] Inventors: Michael Brownlee, Watertown, Mass.; Anthony Cerami, Flanders, N.J.

[73] Assignee: The Rockefeller University, New York, N.Y.

[21] Appl. No.: 62,484

[22] Filed: Jul. 31, 1979

[51] Int. Cl.$^3$ ............ A61K 37/26; C07C 103/52
[52] U.S. Cl. ................................. 424/178; 260/112.7
[58] Field of Search ............... 424/178, 177, 19; 260/112.7

[56] References Cited

U.S. PATENT DOCUMENTS 3,847,890 11/1974 Green et al. .................. 260/112.5
4,003,792 1/1977 Mill et al. ........................ 195/63

OTHER PUBLICATIONS

*Technology Review*, vol. 81, #7, Jun., Jul. 1979.
*Wall Street Journal*, May 25, 1979.
*J. Biol. Chem.*, 253, 2070, (1978).
J. Biol. Chem., 252, 7678, (1977).
Gray, *Arch. Biochem. Biophys.*, 163, 426, (1974).

*Primary Examiner*—Frederick E. Waddell
*Attorney, Agent, or Firm*—Oblon, Fisher, Spivak, McClelland & Maier

[57] ABSTRACT

A process and system for controlled delivery of a biologically active substance to an animal body fluid which comprises contacting fluid with a reversible complex of a conjugate (1) and a binding macromolecule (2), wherein the conjugate (1) comprises a biologically active portion which is intended to be proportionately released into a body fluid stream in response to varying concentration levels of a component of the body fluid stream, and a complexing substrate portion which conjugates with the biologically active portion and which is characterized by affinity to the binding macromolecule (2), competitively or non-competitively with the variable component of the body fluid; thereby causing the component present in the body fluid to complex to the binding macromolecule and thus releasing the conjugate (1) therefrom into the fluid.

The process and system are particularly applicable for the glucose-controlled release of insulin and other hypoglycemic agents in the treatment of diabetes.

15 Claims, 3 Drawing Figures

METHOD AND SYSTEM FOR THE CONTROLLED RELEASE OF BIOLOGICALLY ACTIVE SUBSTANCES TO A BODY FLUID

BACKGROUND OF THE INVENTION

1. Field of the Invention

The present invention relates to a chemical method for the controlled release and delivery of biologically active substances to body fluids.

2. Brief Description of the Prior Art

The use of systems for the slow delivery of medications is known in the art. These systems have been suggested for a wide range of diseases where accurate control of the concentration of released agent is not necessarily critical.

Most "controlled-release" systems known to the prior art however (see e.g. Sears, U.S. Pat. No. 4,145,410, who shows drug release from capsules which are enzymatically labile) are incapable of releasing medication at intervals and concentrations which are in direct proportion to the amount of a metabolite present in the human body. The delivery or release of drug in these prior art systems is thus not literally "controlled", but is simply a slow release, independent of external or internal factors.

For example, although injectable insulin has been available for the treatment of diabetes mellitus for over fifty years, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches to develop a more physiological insulin delivery system have been suggested.

Metas et al (Diabetes 25, 785 (1976)) describe the transplantation into a diabetic animal, of pancreatic tissue from a healthy animal. The transplanted tissue provides a ready source of insulin whose release is controlled primarily by the level of glucose in the blood. This approach has only succeeded with highly inbred strains of animals, however, since tissue rejection otherwise becomes a limiting factor. Obtaining sufficient quantities of acceptably pure islet tissue for future clinical applications also poses significant problems.

Chick (Science, 187, 847 (1975)) avoids the problem of tissue rejection by culturing pancreatic islets on the outside of semipermeable tube-shaped membranes, bundles of which are enclosed by a cylindrical shell. Blood flows through the inner tubes when the system is interposed into the circulation of an animal providing nutrients to the cells. Glucose and insulin pass across the membrane, while larger immunologically active substances remain inside. The use of cultured tissue however implies that the system is only viable for short periods of time. Mechanical problems, such as clogging of the inner tubes by blood also prevent its extensive use.

Soeldner et al (NIH publication No. 76-854 (1976), pp 267 describe a glucose senstive electrode which utilizes immobilized glucose oxidase to produce electric current inversely proportional to the blood glucose level. Glucose oxidase is a very unstable enzyme in this system, and thus limits the use of such an electrode.

Colton et al (Transplantation and Clinical Immunology, X 165-173, Amsterdam, 1978) discuss a system which would eventually include an electronic glucose sensor, an insulin reservoir and pump, and electronics connecting the two. If the sensor finds glucose levels rising, an appropriate amount of insulin would be pumped into the bloodstream—automatically. This system utilizes a platinum electrode catalyst for oxidizing glucose in the sensor. This results in less specific electrodes which show interference with other metabolites and so cannot be used with reliability.

All of these prior art systems take into account the critical relationship between the blood glucose levels and insulin released, and thus attempt to provide the necessary feedback response which would allow the release of insulin to be controlled directly by the amount of blood sugar present at any particular time. However, the systems suffer from a general lack of reproducibility, long-term effectiveness and reliability. None of them have been put into extensive use because of this. A reliable feedback system which does not depend on the use of electrodes or transplanted tissue has not yet been developed. The use of such a simple internally controlled system would greatly expand the use of controlled-release medications. It would be particularly useful in the feedback controlled release of other hormones such as somatostatin, and of modified pharmocological compounds such as enzyme inhibitors and hypoglycemic agents.

SUMMARY OF THE INVENTION

It is therefore an object of the invention to provide a safe and reliable feedback controlled-release drug delivery system.

Another object of the invention is to provide a drug release system which is internally controlled. Still another object of the invention is to provide a controlled drug release system for hormone deficiency diseases.

A further object of the invention is to provide a method for periodically and controllably delivering drugs, especially hormones, to human biological fluids.

These and other objects of the invention have been attained by providing a process for feedback controlled delivery of a biologically active substance to an animal body fluid which comprises contacting said fluid with a reversible complex of a conjugate (1) and a binding macromolecule (2), wherein said conjugate (1) comprises a biologically active portion which is intended to be proportionately released into a body fluid stream in response to varying concentration levels of a component of said body fluid stream, and a complexing substrate portion which conjugates with said biologically active portion and which is characterized by affinity to said binding macromolecule (2) competitively or noncompetitively with said variable component of said body fluid; thereby causing the component present in said body fluid to complex to said binding macromolecule and to release said conjugate (1) therefrom into said fluid.

The objects of the invention have also been attained by providing a process for the controlled delivery of a biologically active hypoglycemic substance to a glucose containing human body fluid which comprises contacting said fluid with a reversible complex of (1) a biologically active hypoglycemic substance which is a conjugate between a carbohydrate and a hypoglycemic agent, and (2) a binding macromolecule having affinity for glucose and for the carbohydrate portion of said conjugate (1); thereby causing the glucose present in said fluid to complex to said binding macromolecule and to release said conjugate into said fluid.

Other objects of the invention have also been attained by providing: a controlled release medication system which comprises a reversible complex of (1) a biologically active hypoglycemic substance which is a conjugate between a carbohydrate and a hypoglycemic agent and (2) a binding macromolecule having affinity for glucose and for the carbohydrate portion of said conjugate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 2:
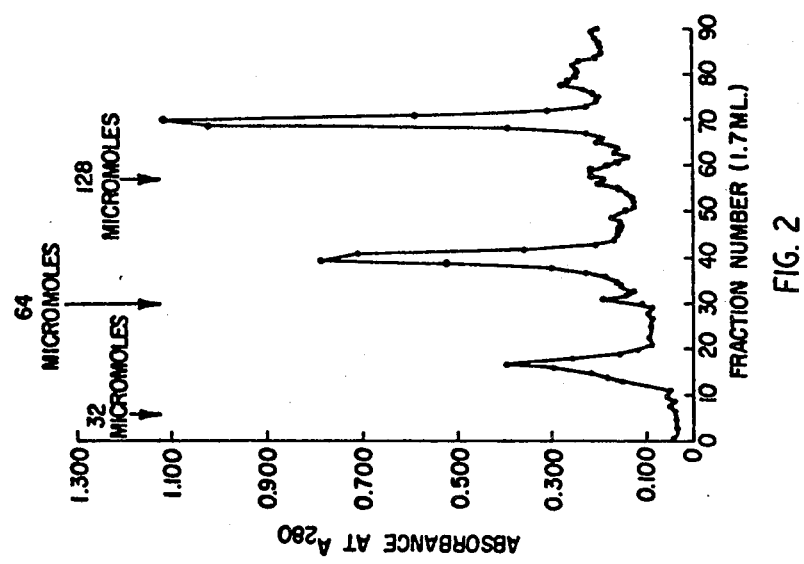
FIG. 2 is the elution profile from a column of immobilized concanavalin A of a maltose-insulin in the presence of pulses of increasing glucose concentration.

The drug delivery system of the present invention comprises a reversible non-covalent complex (B:A-C) between a binding macromolecule (B) and a conjugate of a biologically active substance (A) with a complexing substance (C). The conjugate (A-C) contains a biologically active portion (A) and a complexing portion (C). Equations (1) and (2) show a first embodiment for the operation of the system. This embodiment will be called *directly competitive* in analogy to the well-known kinetic system of competitive inhibition for enzymes (Mahler and Cordes, Biological Chemistry, 2d Edition (1971) pp 295–297):

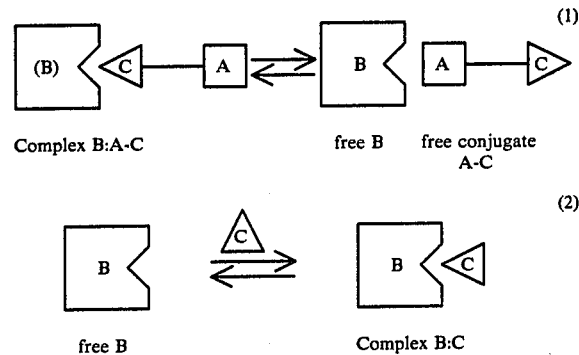

The complex B:A-C is initially in reversible chemical equilibrium with the separated components B and A-C (eq. 1). The binding site of B can only recognize molecules of shape C, either when these are free in solution or when they are coupled to another component such as in conjugate C-A. The degree of association of B with conjugate A-C is ideally very high, so that when no or little C is present independently, the system lies mostly on the B:C-A side of the equilibrium (1), and there are very few free, unassociated B molecules present in solution (eq. 1). However when the concentration levels of C increase in the system, the molecules of C start competing for the available binding sites on B and the equilibrium represented by equation (2) becomes more important. The few unassociated binding molecules B (which are always present) enter into complexation with C and because of the law of mass action, this event causes other B:A-C complexes to become dissociated. In this fashion, the molecules of conjugate A-C are released into the medium when the concentration of free C increases in the medium. Through the intermediacy of binding molecule B, the free concentration of C regulates and controls the appearance of free conjugate A-C in the medium. It is unnecessary that free C and the complexing portion of conjugate A-C corresponding to C, be molecularly exactly identical. It is only necessary that both show complexing affinity for binding molecule B, that they be capable of forming reversible complexes therewith, and that they displace each other from B as a function of concentration, according to the equilibria represented by equations (1) and (2). A system where free C and conjugated C are not identical can therefore also be used in the present invention and is represented by the following equations (3) and (4):

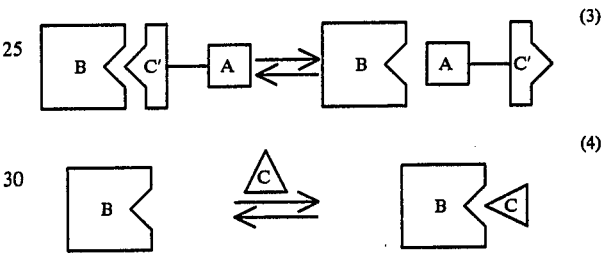

Conjugate A-C' in equation (3) is recognized by B although complexing portion C' is, in overall structure, different than C. The *recognition sites* of both C and C' molecules are, however, exactly alike. C and C' bind at the same site and displace each other from the site.

A second embodiment of the system which is useful in the present invention is one wherein the displacement of conjugate A-C (or A-C'), or more precisely, the blocking of the available site on B for its complexation therewith occurs non-competitively. In this embodiment, B has two sites, one of which complexes with conjugate C-A or C'-A, and the other one with free C. The binding sites are structually different but they interact by negative feedback. When C binds at its own site, this binding causes the second site, which is the site for C-A or C'-A, to change structurally so that its affinity for the conjugate is decreased. Such an embodiment is represented by equation (5):

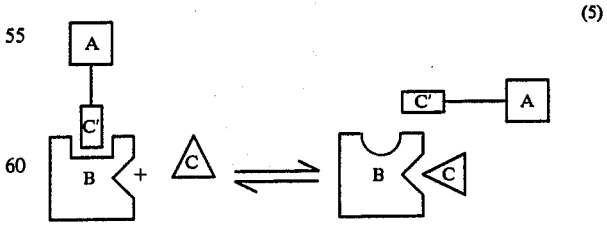

In the absence of fluid component C, the affinity of B for conjugate A-C' is high. The A-C' conjugate is therefore complexed with B. In the presence of C however, the affinity of B for A-C' is much lower, and A-C' is released into the medium. In this second Embodiment, the concentration levels of free C directly control the release of conjugate A-C' into the body fluid. This manner of operation of the system is called *non-competitive* in analogy to the type of enzyme inhibition called non-competitive inhibition (Mahler and Cordes, Biological Chemistry, 2nd Edition, pp 295-298 (1971)).

Binding macromolecule B can be any of a number of well-known macromolecular entities which exhibit molecular recognition and reversible binding of other micro-or macromolecules. B is preferably a natural binding protein, such as an antibody, an enzyme, a regulatory protein, a drug receptor site or the like. It is also possible to use synthetically modified binding molecules, such as chemically modified proteins. Such modified proteins sometimes have increased or decreased affinities for their substrates when compared to their natural unmodified counterparts. By 'macromolecule' is also meant a conjugate of a smaller molecule which shows binding characteristics, with a larger polymeric molecule which, by itself does not. The polymeric molecule would therefore serve as support for the binding smaller molecule and the whole arrangement would therefore be a binding macromolecule. By choosing the appropriate binding macromolecule it becomes possible to control the nature of the released therapeutic drug and its release concentrations. Among examples of binding proteins B, antibodies and lectins are the most preferred. Antibodies can be prepared and purified from animals in standard fashion (Eisen, H. N. "Immunology", Harper & Row, 1974). Antibodies have the advantage of being induceable in an animal by challenge with an appropriate antigenic agent. Since this agent can be chosen from any chemical family e.g., amino acids, carbohydrates, their respective polymeric derivatives, or the like, the resulting antibodies may have a wide range of binding specificity and affinity. Lectins are also particularly useful in this invention. Lectins are carobohydrate-binding proteins of plants and animals with a wide variety of specificities for carbohydrates, (Lis et al, Ann. Review of Biochemistry, 42, 541 (1973); I. J. Goldstein and C. E. Hayes, Adv. in Carbohydrate Chemistry and Biochemistry, Vol. 35, R. S. Tipson and D. Horton, eds. (Academic Press, New York, 1978, pp. 128-341), herein incorporated by reference). For example, concanavalin A, a Jack Bean lectin, has specificity for $\alpha$-D mannopyranose and $\alpha$-D glucopyranose; soybean lectins are specific for $\alpha$ and $\beta$-D-N-acetylgalactosamine and $\alpha$-D-galactose units and wheat germ lectin is specific for $\beta$-D-N-acetyl glucosamine.

Preferably, a manno-oligosaccharide containing from 2 to 7 (1→2) $\alpha$-D-mannopyranosyl residues is used as the carbohydrate.

The molecular complexation reaction between binding macromolecule B and molecule C, or the C or C' portion of conjugate A-C, has to be reversible and non-covalent. This bonding between B and C (or B and A-C) is caused by non-covalent forces such as hydrophobic, ionic, hydrogen bonding forces and the like. These interactions have been well studied in the art and their effects on molecular affinity and recognition are described, for example in Korolkovas et al, "Essentials of Medicinal Chemistry", pp 44-81 Wiley, 1976, which is herein incorporated by reference. Such reversible interactions are exemplified by the interaction between an enzyme and its substrate or a competitive inhibitor thereof; and antibody with its antigen, or a drug receptor site and its drug.

The functional relation between component C present in the body fluid and the biologically active agent A is very important. The biologically active conjugate A-C (or A-C') is released in proportionate amounts to the levels of component C present in the body fluid. Agent A therefore can be a hormone-type substance which directly regulates the levels of C in the fluid, by for example, causing a decrease of the levels of C. Agent A, however need not be directly functionally related to component C but only indirectly. In such case, increasing levels of C in the fluid would release conjugate A-C (or A-C') which then, via its biologically active portion A, will act on a biological system unrelated or only indirectly related to component C. The system will then release A-C into the fluids as a function of the concentration of any metabolite being "monitored". In a preferred embodiment, however, A is a hormone or hormone-like substance and C is a metabolite participating in a feedback regulatory loop with A.

Hormones are substances secreted by endocrine glands or in tissues and released into the bloodstream, by which they are transported to other tissues where, by selectively binding to specific receptors, they exert their effects. Hormones possess a wide range of chemical structures: peptides, steroids, derivatives of amino acids and derivatives of fatty acids. Hormones are glandular or tissue-originated. Among the common glandular hormones useful with the system of the present invention are the pituitary and hypothalamic polypeptide hormones such as oxytocin, arginine-vasopressin, lysin-vasopressin, adrenocorticotropin (ACTH), follicle-stimulating hormone (FSH); somatotropin (GH), luteinizing hormone (LH), melanocyte-stimulating hormone (MSH), prolactin, thyroid-stimulating hormone (TSH); the parathyroid hormone; calcitonin; the hormones of the pancreas such as insulin; glucagon and somatastatin, the adrenal cortical hormones such as mineralocorticoids as aldosterone and desoxycorticosterone, glucocorticoids as cortisone and hydrocortisone, sexual hormones as androgens, anabolic steroids, estrogens, progestagens. Among the common tissue hormones useful in the method of the present invention are, for example, histamine, norepinephrine, serotonine, prostaglandins, prostacyclins, and thromboxanes. Any of these hormones or their biologically active analogs or derivatives can be used in the preparation of the A-C conjugate of the present invention.

The coupling molecule C is the substance whose varying levels will proportionately release active conjugate A-C (or A-C'). In a preferred embodiment, C is a fluid component whose levels are regulated by A-C. In such case, C has to be in functional relation to molecule A, since as explained above its levels are regulated by A. Most preferably C is chosen so that a feedback loop exists between C and A; i.e., when the levels of C increase in the blood, the levels of A increase under normal circumstances, thus returning the level of C, and in turn A, to their equilibrium positions.

It is crucial that after the chemical coupling of C to A, the complexing portion of the conjugate A-C corresponding to C, preserve the affinity of the original C to the binding macromolecule B and that it be displaced therefrom by increasing concentrations of free C. Furthermore it is useful to choose or chemically modify C in such manner that it will be easily chemically coupled to A, to yield conjugate A-C. Examples of coupling molecules C (given with their regulatory active substances) are: glucose (regulated by insulin and also by other hypoglycemic agents such as sulfonylureas and biguanides); calcium (regulated by calcitonin); cortisol (regulated by ACTH); progesterone (regulated by LH): testosterone (regulated by LH); thyroid hormones (regulated by TSH); prolactin (regulated by prolactin-release inhibiting hormone); growth hormone (regulated by growth hormone releasing-inhibiting hormone); electrolytes (regulated by mineralocorticoids).

The coupling between A and C can be carried out directly by using appropriate functional groups on both molecules or by using a bridging or spacer group between them. Nucleophilic groups on one component, such as free —OH or —NH$_2$ or —SH can be reacted with electrophilic groups on the other component, such as esters, ketones, aldehydes and the like, to give covalent adducts. The coupling between a peptide containing free amino groups and a carbohydrate containing aldehyde groups can be carried out to yield (an imine

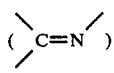

which, in the presence of a reducing agent such as NaBH$_4$, KBH$_4$, NaCNBH$_3$ will give primary or secondary amines. This type of reaction is well exemplified in the prior art, as demonstrated by Gray, G. R., Archives of Biochemistry and Biophysics, 163, 426 (1974) or by Wilson, G. J., of Biol. Chemistry 253, 2070 (1978), both of which are herein incorporated by reference. Another possible coupling reaction is that between free amines on proteins and ester functions on proteins or carbohydrates, to give amides. In the latter case of course, the naturally occuring free carboxylic acids of the protein or carbohydrate have to be chemically esterified first, as by reaction with a diazoalkane such as diazomethane.

The final bond between A and C has to be stable and irreversible and is, most preferably, covalent.

The properties of the conjugate A-C or A-C' are such that it should retain both the reversible affinity and binding characteristics of C and the biological activity of A. Its properties are therefore a composite of those of both its constituents. The choice of appropriate coupling partners and coupling methods are critical. Chemical attachment of the type required by the present invention might lead to a great or even total loss of binding or of regulatory activity, or both. It is crucial that none of these activities be lost after coupling.

According to the process of the present invention the B:A-C (or B:A-C') complex is brought into intimate contact with the physiological human fluid to be treated. The controlled release of active conjugate A-C (or A-C') begins when the amount of free C in the fluid contacting the complexes reach a given critical high level. Virtually no active conjugate is released when the levels of free C fall below the critical level. It is also possible to simultaneously contact the body fluid with complexes between B and active conjugates A-C', A-C" and A-C"' wherein these conjugates have different affinity towards B. In this way increasing levels of C in the fluid would release a steadily increasing amount of active conjugate. Still another possibility is to contact the body fluid with complexes between B and A-C, A'-C and A"-C, where A, A' and A" represent biologically active portions of the conjugate exhibiting different biological activities. In this mode, increasing levels of fluid component C will release two or more different substances which exhibit different biological effects.

By appropriate choice of B, A and C and of active analogues thereof, the possibility exists of treating a wide variety of diseases with individualized drug-delivery profiles.

The system of the present invention is ideally suited for use in externally or internally implanted devices, such as insulin pumps or the like. The complex B:A-C may be present in a semipermeable or porous tube or fiber, which is brought into contact with human fluid such as plasma. The pores of the tube or device are chosen so that the complex and the binding molecule B cannot pass therethrough and are 'trapped' inside. The pores however are permeable to conjugate A-C and free component C. When the concentration of component C in the plasma reaches critical levels, conjugate A-C (or A-C') is released into the plasma. It passes freely through the pores of the tube or fibers and is assimilated into the body, while the B:C complex remains trapped behind. Exchanging the solution within the tubes periodically by fresh solution of B:A-C complex, simply replenishes the supply of drug. Another embodiment of the invention is to fix the binding macromolecule B covalently either directly, or via a spacer or bridging group, to the tube itself. The techniques of solid-state immobilization of enzymes and other proteins on resins, films, test tubes, glass beads and the like are well known (see e.g., Zaborsky, C. "Immobilized Enzymes" CRC Press, Cleveland, 1973; Axen et al U.S. Pat. No. 3,645,852; Kraemer et al, U.S. Pat. No. 4,039,413). In this fashion, 'cartridges' of a semiporous, semipermeable film such as cellulose can be prepared which contain covalently bound B in the form of its reversible complex B:A-C. Upon contact with body fluid and subsequent exchange of A-C by C, the cartridge becomes 'spent' and can be readily replaced by a fresh one. The spent cartridges can then be recycled by extensive dialysis against solution containing conjugate A-C.

In a particularly preferred embodiment, this invention relates to a system for the delivery of active hypoglycemic agents, preferably insulin, to the bloodstream of patients with diabetes mellitus. Diabetes mellitus is a hereditary disease characterized by the relative or absolute deficiency of insulin. Insulin is a polypeptide hormone made of 2 chains of amino acids, molecular weight 6000. It is synthesized, stored and released from the pancreas primarily in response to blood glucose levels. Insulin carries out a variety of physiological functions such as for example activation of transport systems for glucose and of certain enzymes involved in increased glucose utilization, glycolysis, glycogenesis and lipogenesis. Absence of insulin thus causes an increase in the blood levels of glucose (hyperglycemia).

The system of the present invention wherein A is an active hypoglycemic agent, C is glucose or an actively binding analogue thereof with complexing characteristics similar to those of glucose, and B is a carbohydrate-binding molecule, is readily applicable to the treatment of hyperglycemia. In particular, when the conjugate A-C is prepared from insulin and oligosaccharides such as maltose, and maltose-triose, the resulting conjugate retains hormonal activity. Any of the oligosaccharides described in Lis et al, Ann. Rev. of Biochemistry, 42, 541 (1973), can be used. Furthermore, the oligosaccharide-insulin conjugate binds to a lectin such as concanavalin A and can be displaced therefrom by solutions with increasing glucose content. Various hypoglycemic agent-conjugates, complementary to the major combining sites of the lectins, can be synthesized and the products are stable. Since lectin binding affinity for various saccharides varies more than ten-fold, a mixture of different high-and low-affinity semisynthetic conjugates can be combined to produce clinically desirable elution profiles. A number of active insulin derivatives have been prepared (Ellis, M. S., et al, Diabetologia 11:340, 1975; Tompkins, C. V. and Sonksen, P. H., Clin. Sci. and Mol. Med. 50:31, 1976; Darby, S. C. et al, Diabetologia 15:403, 1978). These derivatives and/or analogs can of course be used in the process of the present invention. It is also possible to synthesize other glycosylated hypoglycemic agents such as glycosylated sulfonylureas and biguanides (Korolkovas et al, Essentials of Medicinal Chemistry, p. 605 (Wiley, 1976)). Glucose-activated release of these agents is then carried out according to the same system. Another application, is the preparation of glycosylated derivatives of somatostatin. This would provide glucose-controlled inhibition of the excessive glucagon secretion which is thought to exacerbate diabetic hyperglycemia.

Yet another application of the system, in a mode where agent A is not a hormone involved in the regulation of component C, is for example the release of enzymatic inhibitors in diabetes mellitus. Studies in animals (Winegrad, A. I. et al, In Proceedings of the VIII Congress of the International Diabetes Federation, ed. W. J. Malaisse and J. Pirart, pp. 387–395, Excerpta Medica, Amsterdam), suggest that excessive conversion of glucose to sorbitol by the enzyme aldose reductase may be of etiologic significance in the pathogenesis of several diabetic complications. A variety of inhibitors for aldose reductase has been prepared (Gabbay, K. H., Adv. Metab. Disorders Suppl. 2. New York, Academic Press, 1973, pp. 417–424; Dvornik, D. et al: Science 182:1146, 1973; Varma, S. D. et al, Science 188:1215, 1975; M. J. Peterson et al, Metabolism 28:456, 1979; Kinoshita, J. H. et al Metabolism 28:462, 1979, all of which are herein incorporated by reference) with the purpose of decreasing the levels of activity of the enzyme. Any of these inhibitors could be conjugated to a carbohydrate and used in the system of the present invention. When the levels of glucose increase in the blood, inhibitor-conjugates will be released, decreasing the possibility of damage due to sorbitol.

The synthesis of glomerular basement membrane (GBM) has also been reported to increase with increased levels of blood glucose (Spiro, R. G. and Spiro, M. J. Diabetes 20:641, 1971; Brownlee M. and Spiro, R. G. Diabetes 28:121, 1979). Excessive accumulation of this material is also a cause of damage in diabetes. Conjugating a carbohydrate to an inhibitor of an enzyme involved in the synthesis of GBM (Maragoudakis, M et al, J. Pharm. Exp. Ther. 204:377, 1978, herein incorporated by reference) will then yield a substance capable of use in the process and system of the present invention.

Still another application of the present invention is in the simultaneous release of a combination of hypoglycemic agents. Alburn et al (U.S. Pat. No. 3,912,807) have shown that the combination of somatostatin and insulin is very effective in the treatment of diabetes mellitus. Dietze et al (U.S. Pat. No. 4,150,121) have demonstrated that kinin-insulin combinations are useful in diabetes, and Laborit (U.S. Pat. No. 4,035,486) has shown that guanosine increases glucose utilization in diabetic animals treated with insulin or acetylcholine. The system of the present invention can thus be simply adapted to the glucose-dependent release of drug combinations. For example, it is possible to contact the body fluid with two complexes: a first one comprising a lectin and a conjugate of carbohydrate and insulin, and a second one comprising a lectin and a conjugate of carbohydrate and guanosine. In this fashion raising glucose levels will release both guanosine and insulin into the body fluid.

Having now generally described this invention, a further understanding can be obtained by reference to a specific example which is provided herein for purposes of illustration only and is not intended to be limiting unless otherwise specified.

I. Preparation of a Maltose-Insulin Conjugate

Maltose was incubated with porcine insulin (Lilly) at a Molar ratio of 650:1 for 5 days at 37° C. in 0.1 M sodium phosphate buffer pH 8.0. The incubation was carried out in the presence and absence of 0.25 M sodium cyanoborohydride. Unreacted maltose was removed by gel filtration on Bio-gel P-G and the conjugated insulin was separated by affinity chromatography on a Concanavalin A Sepharose 4B column. Analysis of the product of carbohydrate (phenolsuefuric acid method, Dubois, M. et al, Analyt Chem., 28, 350 (1956)) and for protein (Lowry, O. H., et al, J. Biol. Chem, 193, 265 (1951)) showed that after a 5 day incubation, the derivative contained 1.76 moles of covalently bound carbohydrate per mole of insulin monomer. Since substitution of all three primary amino groups has been reported to result in the loss of hormone activity (Ellis, M. J. et al, Diabetologia, 15, 403 (1978)), a 5 day incubation time was chosen to maximize yield while minimizing loss of biological activity.

The insulin conjugate was stored at 4° C. and was stable for at least seven weeks regardless of whether or not reducing agent had been added.

II. Bioactivity of Maltose-Insulin Conjugate.

The conjugate prepared in I was tested using the blood-glucose depression assay modified from the U.S. Pharmoacopeia (Vol. XVIII, 883–884 (1967)). Preparations varied from 78 to 95% of unmodified insulin bioactivity. The results are given in Table 1.

TABLE 1

| BIOACTIVITY OF MALTOSE-INSULIN DERIVATIVE | | | |
|---|---|---|---|
| | BLOOD GLUCOSE DEPRESSION* | | |
| ANIMAL | Maltose-insulin derivative | Control insulin | p |
| A | 61 mg % | 75 mg % | |
| B | 64 mg % | 70 mg % | |
| C | 66 mg % | 79 mg % | |
| D | 63 mg % | 79 mg % | |
| E | 69 mg % | 64 mg % | |
| F | 74 mg % | 73 mg % | |
| Mean ± S.E.M. | 66.17 ± 1.92 | 73,33 ± 2.35 | <0.1 |

*After an overnight fast, each animal received 0.1mg protein/100gm body weight by subcutaneous injection. Each of the animals served as its own control, receiving the maltose-insulin derivative on day 1, and control insulin on day 2. Blood glucose depression was determined 60 minutes after injection using a Beckman Glucose Analyzer 2.

III. Binding Of Maltose Insulin to Concanavalin A

Figure 1A:
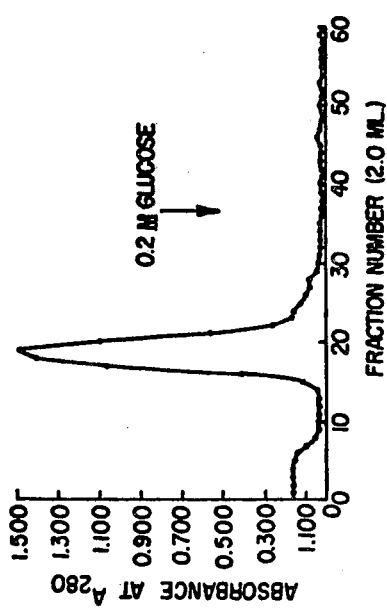
FIG. 1 is the elution profile from a column of immobilized concanavalin A, of insulin (A) and maltose-insulin conjugate (B) in the presence of glucose as eluant (arrows).
Figure 1B:
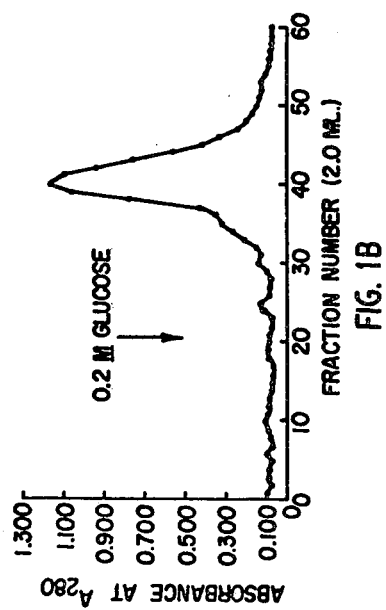

FIG. 1 shows the elution profile obtained from 20 mg of unmodified insulin (A) and maltose-insulin (B) applied to columns (24.0×1.5 cm I.D.) of immobilized Concanavalin A. Initial buffer was 1 mM MgCl$_2$, 1 mM CaCl$_2$, 50 mM NaCl, 25 mM sodium phosphate, pH 7.4. At the point indicated by the arrow, 0.2 M glucose in the column buffer was begun. Fractions (2.0 ml) were collected at a flow rate of 10–15 ml/h. Unmodified insulin did not bind to Concanavalin A. When this material was applied to the lectin, all of the protein was recovered in the buffer wash, and none was eluted by the addition of glucose. In contrast, all of the maltose-insulin derivative was bound to Concanavalin A. None was eluted by the buffer wash, and all of the maltose-insulin derivative could be displaced from Concanavalin A binding sites by a 1,000:1 molar excess of glucose.

FIG. 2 shows the elution profile obtained from 20 mg maltose-insulin derivative applied to a column (12.0×1.5 cm I.D.) of immobilized Concanavalin A. Initial buffer was 1 mM $MgCl_2$, 1 mM $CaCl_2$, 50 mM NaCl, 25 mM sodium phosphate, pH 7.4. Displacement of hormone was accomplished using 1.0 ml pulses of column buffer containing varying amounts of glucose. Glucose content is indicated over the appropriate arrows. Fractions (1.7 ml) were collected at a flow rate of 10–15 ml/h. Glucose-pulse experiments with the lectin-bound maltose-insulin derivative demonstrate that hormone release is a function of the quantity of glucose present.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. A process of treating hyperglycemia which comprises:
    delivering to a glucose containing human body fluid a reversible complex of (1) a hypoglycemically active insulin analogue which is a conjugate between a carbohydrate and an insulin and (2) a lectin having affinity for glucose and for the carbohydrate portion of said conjugate (1); thereby
    causing the glucose present in said fluid to complex to said lectin and to release said conjugate into said fluid.

2. The process of claim 1 wherein said lectin is Concanavalin A.

3. The process of claim 1 wherein said carbohydrate is maltose.

4. The process of claim 1 wherein said reversible complex comprises at least two conjugates of different affinity towards said lectin (2).

5. The process of claim 1 wherein said reversible complex comprises at least two conjugates with different hypoglycemically active portions.

6. The process of claim 5 wherein said two different hypoglycemically active portions are guanosine and insulin.

7. The process of claim 1 wherein said carbohydrate is a manno-oligosaccharide containing from 2 to 7 (1→2) α-D-mannopyranosyl residues.

8. A controlled release medication which comprises:
    a hypoglycemically active amount of a reversible complex of (1) a hypoglycemically active insulin analogue which is a conjugate between a carbohydrate and an insulin and (2) a lectin having affinity for glucose and for the carbohydrate portion of said conjugate.

9. The medication system of claim 8 wherein said lectin is Concanavalin A.

10. The medication system of claim 8 wherein said carbohydrate is maltose.

11. The medication system of claim 8 wherein said reversible complex comprises at least two conjugates (1) having different affinity towards said lectin.

12. The medication system of claim 8 wherein said reversible complex comprises at least two conjugates with different hypoglycemically active portions.

13. The medication system of claim 8 wherein said carbohydrate is a manno-oligosaccharide containing from 2 to 7 (1→2) α-D-mannopyranosyl residues.

14. The process of claim 1 wherein said insulin/carbohydrate conjugate is such that not all three primary amino groups of insulin are substituted by said carbohydrate.

15. The medication of claim 8 wherein said insulin/carbohydrate conjugate is such that not all three primary amino groups of insulin are substituted by said carbohydrate.

* * * * *